(12) United States Patent
Dudda et al.

(10) Patent No.: US 6,245,011 B1
(45) Date of Patent: Jun. 12, 2001

(54) ENDOSCOPIC INSTRUMENT WITH CUTTING TOOL

(75) Inventors: Werner Dudda, Süptiz; Thomas Weller, Tuttlingen; Horst Dittrich, Immendingen, all of (DE)

(73) Assignee: Karl Storz GmbH & Co. KG (DE)

( * ) Notice: Subject to any disclaimer, the term of this patent is extended or adjusted under 35 U.S.C. 154(b) by 0 days.

(21) Appl. No.: 09/347,186

(22) Filed: Jul. 3, 1999

(30) Foreign Application Priority Data

Nov. 4, 1997 (DE) ............................................. 197 48 579

(51) Int. Cl.[7] ....................................................... A61B 1/00
(52) U.S. Cl. ......................... 600/104; 600/106; 600/107; 606/46
(58) Field of Search .................................. 600/104, 106, 600/107; 606/46

(56) References Cited

U.S. PATENT DOCUMENTS

| 3,896,793 | * | 7/1975 | Mitsui et al. ............................ 128/6 |
| 4,245,624 | * | 1/1981 | Komiya ..................................... 128/4 |
| 4,427,000 | * | 1/1984 | Ueda ......................................... 128/6 |
| 4,607,619 | * | 8/1986 | Seike et al. .............................. 128/4 |
| 4,674,500 | | 6/1987 | DeSatnick . |
| 4,841,949 | | 6/1989 | Shimizu et al. . |
| 5,041,124 | | 8/1991 | Kensey . |
| 5,047,043 | | 9/1991 | Kubota et al. . |
| 5,258,026 | | 11/1993 | Johnson et al. . |
| 5,343,853 | * | 9/1994 | Komi ........................................ 128/4 |
| 5,507,764 | * | 4/1996 | Muller .................................. 606/180 |
| 5,624,379 | * | 4/1997 | Ganz et al. ........................... 600/104 |
| 5,651,781 | * | 7/1997 | Grace ..................................... 606/1 |
| 5,702,344 | * | 12/1997 | Silverstein ........................... 600/104 |
| 5,868,663 | * | 2/1999 | Katsurada et al. ................... 600/107 |

FOREIGN PATENT DOCUMENTS

| 27 37 014 A1 | 3/1979 | (DE) . |
| 37 07 403 A1 | 9/1987 | (DE) . |
| 37 41 938 A1 | 6/1988 | (DE) . |
| 197 48 579 A1 | 5/1999 | (DE) . |
| 0 638 279 A1 | 2/1995 | (EP) . |

OTHER PUBLICATIONS

"Die Welt Der Endoskopie," *Proktologie* 5. Ausgabe 1/92.

* cited by examiner

*Primary Examiner*—Linda C. M. Dvorak
*Assistant Examiner*—Jocelyn Ram
(74) *Attorney, Agent, or Firm*—St. Onge Steward Johnston & Reens LLC (57) ABSTRACT

An endoscopic instrument with cutting tool has a shaft for introduction into duct-like body passages such as a rectum, trachea, or esophagus, and has an endoscopic optical system. Arranged in said shaft is a cutting tool, for introducing an incision in the circumferential direction of said body passage, that by way of a displacement mechanism can be extended out of said shaft beyond the periphery of said shaft and retracted back thereinto.

28 Claims, 5 Drawing Sheets

ENDOSCOPIC INSTRUMENT WITH CUTTING TOOL

CROSSREFERENCE OF PENDING APPLICATION

This application is a continuation of pending international application PCT/EP 98/06898.

BACKGROUND OF THE INVENTION

The present invention relates to an endoscopic instrument with cutting tool, having a shaft for introduction into duct-like body passages such as the rectum, trachea, or esophagus, and having an endoscopic optical system.

An instrument of this kind is known from the company brochure of Karl Storz GmbH & Co., Tuttlingen: "STORZ, THE WORLD OF ENDOSCOPY, PROCTOLOGY, FIFTH EDITION 1/92," 1992, page PRO 2. The instrument described there is a proctoscope.

A proctoscope is used in medicine for inspection of the anal duct and the lower portion of the rectum of a patient. For this purpose, the proctoscope is introduced into the anal duct with an obturator, inserted into a tube, whose distal end is of beveled configuration. The obturator is then pulled back out of the tube, and instead an insert with lateral windows is introduced into the tube; with this, the anal duct can be inspected via an endoscopic optical system in order to detect proctological diseases.

If a tumor in the intestinal wall is detected during the proctological examination, it must then be surgically removed. For surgical removal of deep tumors in the lower rectum, it is necessary to introduce a circular incision into the intestinal wall in the circumferential direction. This operation is very difficult and time-consuming and cannot be performed with the conventional proctoscope alone, instead requiring a special surgical incision instrument.

The invention is not limited, however, to a proctoscope of this kind. Further comparable endoscopic instruments that are introduced into duct-like body passages in order to inspect the body passage are the rectoscope, esophagoscope, and tracheoscope. Rectoscopes are also introduced into the bowel in order to inspect the bowel. An esophagoscope is used to inspect the esophagus, and a tracheoscope to inspect the bronchial tubes. In the case of these endoscopic instruments as well, the only ones available at present are those with which the corresponding body passages can be inspected, but with which it is not possible to introduce a circular incision into the wall of the respective body passage.

DE-A-27 37 014 discloses an endoscope for slitting through urethra constrictions. The endoscope has a shaft tube in which a knife for slitting through the constriction is provided distally. The knife can be pivoted out about a transverse axis through a longitudinal slot in the shaft by way of a longitudinally displaceable wedge arranged distally from it, using a proximal handle via a wire pull, from a rest position in which the knife lies recessed in the shaft. The knife is used to make an incision in the longitudinal direction of the shaft axis.

Also known from U.S. Pat. No. 4,674,500 is a surgical incision instrument that is used in arthroscopy and in those surgical procedures in which access to the surgical site is limited or difficult. This instrument accordingly has a very thin shaft, bent over laterally at the distal end, in which a knife blade is received displaceably in the longitudinal direction of the shaft. The knife is of bendable configuration, so that by being advanced, it can be pushed out of the laterally curved distal end of the thin shaft in order to make an incision. This instrument with a curved shaft is not suitable, however, for use in a duct-like body passage.

It is therefore the object of the invention to improve an endoscopic instrument of the kind cited initially in such a way that it is possible with the instrument not only to perform an inspection of the respective body passage, but also to surgically remove a tumor by introducing an incision into the wall of the body passage.

SUMMARY OF THE INVENTION

According to the present invention, this object is achieved by an endoscopic instrument, having a shaft for introduction into a duct-like body passage, said shaft having a periphery, an endoscopic optical system extending through said shaft, a cutting tool arranged in said shaft, wherein said cutting tool is movable between a retracted position where said cutting tool is completely disposed inside said shaft and an extended position where said cutting tool extends out of said shaft beyond said periphery of said shaft, and wherein in said extended position, said cutting tool is arranged for introducing an incision in said body passage in circumferential direction of said body passage, and a displacement mechanism for moving said cutting tool between said retracted position and said extended position.

According to another aspect of the present invention, a method for introducing an incision into a wall of a duct-like body passage comprises the steps of providing an instrument having a shaft for introduction into said duct-like body passage and a cutting tool disposed within said shaft that by way of a displacement mechanism can be extended out of said shaft beyond a periphery of said shaft, introducing said instrument with said cutting tool in its retracted position into said body passage such that said periphery of said shaft is positioned at a portion of said wall where said incision is to be introduced, extending said cutting tool beyond said periphery of said shaft by way of said displacement mechanism whereby said cutting tool engages said wall, and turning said shaft about its longitudinal axis thereby introducing said incision into said wall of said body passage in circumferential direction.

Because a cutting tool is integrated into the instrument according to the present invention in the shaft, it can be used not only for inspection purposes but also as a surgical instrument for cutting out, for example, tumors. In this context, the operation can advantageously be observed and monitored with the endoscopic optical system. Because the cutting tool can be extended out beyond the periphery of the shaft, the required incision can be made, for example in the case in which the instrument according to the present invention is configured as a proctoscope, in the circumferential direction of the intestinal wall, by rotating the shaft, with the cutting tool extended, about its longitudinal axis; as a result, the cutting tool introduces into the intestinal wall an incision to a depth corresponding to the extension span, or corresponding to the width to which the cutting tool projects out beyond the periphery of the shaft. Because the cutting tool can be retracted into the shaft and thus can be recessed, the shaft can readily be introduced into the body passage without injuring the wall of the passage with the cutting tool as the instrument is introduced. Blades for mechanical cutting, wire electrodes for cutting with high-frequency current, ultrasonic cutting applicators, or lasers can be used as cutting tools. "Retractable" is understood to mean, for the purposes of the subject matter of the present invention, for example a radial movement or an outwardly pivoting or bending movement of the cutting tool, or also the activation, enabling, or expansion of the working radius of a laser cutting tool.

The object of the invention is completely achieved in this manner.

In a preferred embodiment, the cutting tool is lockable in the maximally extended position and in the retracted position.

Because the cutting tool can be locked in the maximally extended position, the incision to be performed can be made safely, with no danger that the cutting tool will be pushed back into the shaft during cutting. The incision can thus be made reliably. The fact that the retracted position can be locked guarantees that the cutting tool does not prematurely extend upon introduction of the shaft into the body passage and, in the case where the instrument is used for inspection purposes, does not extend inadvertently and injure, for example, the intestinal wall. The reliability of the instrument according to the present invention is thus improved.

In a further preferred embodiment, the cutting tool is lockable in a plurality of positions of different extension spans between the retracted and maximally extended positions.

The advantage of this feature is that with the instrument according to the present invention, in the case of the removal of, for example, a tumor, incisions of different depths can be introduced into the wall of the body passage depending on the requirements, thus ensuring that the cutting tool is locked at its preset extension span until a new extension span is set in order to attain a different incision depth.

In a preferred exemplary embodiment, the cutting tool can be extended radially.

A cutting tool that can be extended radially has the advantage that the cutting tool can be applied at an exactly defined point on the periphery of the wall of the body passage where the incision is to begin. For that purpose, the shaft is moved, with exactly the peripheral location at which the cutting tool emerges from the shaft, to that point; upon extension, the cutting tool then engages into the wall of the body passage exactly at that point. The precision of the instrument according to the present invention is thus increased.

In a further preferred embodiment, the displacement mechanism is actuable from the proximal end of the instrument.

The advantage of this feature is that the surgeon can easily actuate extension and retraction of the cutting tool, thus improving the handling of the instrument according to the present invention.

In a further preferred embodiment, the displacement mechanism for locking the cutting tool can be click-stopped.

The displacement mechanism thus provides not only for extension and retraction of the cutting tool, but also simultaneously for locking of the cutting tool. The advantage thereby achieved is that no further means need to be provided for locking the cutting tool. A click stop moreover has the advantage on the one hand that it is rapidly releasable, and on the other hand that the cutting tool can be rapidly and securely locked.

In a preferred exemplary embodiment, the displacement mechanism has a proximally actuable actuation rod whose distal end coacts with the cutting tool.

The advantage of this feature is that the physician using the instrument can actuate the cutting tool at the proximal end of the instrument according to the present invention, thereby improving the handling of the instrument according to the present invention.

It is preferred in this context if the actuation rod is rotatable, and the cutting tool can be extended and retracted by rotating the actuation rod.

A displacement mechanism having a rotatable actuation rod has the advantage that a displacement mechanism of this kind is easy to operate.

It is furthermore preferred if the proximal end of the actuation rod has two wheels that are rotatable relative to one another, the one wheel being joined nonrotatably to the actuation rod and the other wheel being attachable nonrotatably on the shaft.

The advantage of this feature is that the actuation rod with the wheel that is attachable and nonrotatable on the shaft can be immobilized on the shaft, while the wheel joined nonrotatably to the actuation rod can be used to extend and retract the cutting tool by rotation. The wheel that is attachable nonrotatably on the shaft simply needs to be released for removal of the actuation rod from the shaft, and thus allows easy disassembly of the instrument according to the present invention.

It is further preferred in this context if one or more ball catches are arranged between the wheels.

The ball catches advantageously create a mechanically simple click-stop mechanism for locking the cutting tool.

As an alternative thereto, it is preferred if the actuation rod is axially displaceable and the cutting tool can be extended and retracted by displacing the actuation rod.

This feature likewise results in an easily operated displacement mechanism.

In a preferred exemplary embodiment, the actuation rod is joined to the cutting tool by way of an axially detachable plug-in connection.

The advantage of this feature is that the actuation rod and cutting tool can easily be joined to one another by inserting the actuation rod into the shaft; and conversely, for replacing the cutting tool, the actuation rod simply needs to be pulled back, thereby releasing the cutting tool.

In a further preferred embodiment, a lens of the endoscopic optical system is arranged in the region of the cutting tool in such a way that the cutting tool is observable through the endoscopic optical system.

Because of this design feature, the surgeon can observe and monitor both the extension and retraction of the cutting tool, and the cutting operation itself.

In a further preferred embodiment, in the extended position the cutting tool can be caused to oscillate by way of a drive system.

The oscillating back-and-forth movement of the cutting tool advantageously results in an enhancement of the cutting effect of the cutting tool.

In a further preferred embodiment, an indicating means for the extension span of the cutting tool is provided.

The advantage of this feature is that the physician using the instrument can monitor the extension span of the cutting tool and set it exactly to the respective cutting depth. This is advantageous in particular because although the physician can observe the cutting tool through the endoscopic optical system, the cutting tool is imaged in magnified or reduced fashion depending on the endoscopic optical system used and its position with respect to the cutting tool, so that the physician might erroneously set an inappropriate extension span. The indicating means prevents such an error.

It is preferred in this context if the indicating means is provided on the cutting tool.

This can be achieved, for example, by way of a scale on the cutting tool, which can then be read through the endoscopic optical system.

In a further preferred embodiment, the indicating means is provided on the displacement mechanism.

This feature also makes possible exact monitoring of the extension span of the cutting tool. It is also entirely possible to provide an indicating means on both the cutting tool and the displacement mechanism.

In a preferred exemplary embodiment, the cutting tool is a blade whose cutting edge is oriented in the circumferential direction of the shaft.

The use of a blade as the cutting tool advantageously represents a mechanically simple, stable, and economical embodiment of the instrument according to the present invention, with which the desired circular incision in the circumferential direction of the wall of the body passage can be made.

In a preferred embodiment, the blade tapers to a tip in the region of the cutting edge.

The advantage of this feature is that the blade, upon extension out of the shaft, can easily penetrate with its tip into the wall of the body passage.

In a further preferred embodiment, the blade has an elongated hole into which engages a pin arranged at the distal end of the actuation rod eccentrically with respect to its longitudinal axis.

This feature advantageously creates a particularly simple kind of plug-in connection between the actuation rod and the blade. As a result of the eccentric arrangement of the pin, a rotary movement of the actuation rod is converted into a radial movement of the blade. A particularly simple displacement mechanism for retracting and extending the blade for the instrument according to the present invention is created in this manner.

It is further preferred if the blade is received in a recess of the shaft that is open toward the periphery of the shaft and extends substantially radially.

In the retracted state, the recess completely receives the blade. The recess moreover represents a mechanically simple radial guide during retraction and extension of the blade. A further advantage is the fact that while cutting, the blade is securely held in the recess in the cutting direction.

In a further preferred embodiment, the shaft is configured as an insert that can be slid into a tube.

This has the advantage that first of all the tube can be introduced into the body passage, and then the insert for making the incision, and optionally other instruments, can be introduced into the tube, for example to remove the cutaway tissue.

It is preferred in this context if the insert is attachable rotatably in the tube.

This feature has the advantage, for example when the instrument is configured as a proctoscope, that the insert can be secured axially to the tube, but at the same time the insert can be rotated in the tube in order to inspect the intestinal wall and to make the incision in the intestinal wall.

In a further preferred embodiment, the cutting tool is a cutting wire.

In this embodiment of the instrument according to the present invention, the incision is effected by high-frequency current.

In a further preferred embodiment, the shaft is flexible.

The advantage of this embodiment is that the shaft can adapt to the anatomical profile of the body passage into which it is introduced.

Further advantages are evident from the description below of the appended drawings.

It is understood that the features mentioned above and those yet to be explained below can be used not only in the respective combinations indicated, but also in other combinations or in isolation, without leaving the context of the present invention.

BRIEF DESCRIPTION OF THE DRAWINGS

An exemplifying embodiment of the invention will be described in more detail hereinafter with reference to the drawings, in which:

FIGS. 7a) and 7b) show the functional principle of the displacement mechanism for retracting and extending the cutting tool.

DETAILED DESCRIPTION OF A PREFERRED EMBODIMENT

FIGS. 1 through 5 depict an endoscopic instrument that is embodied as a proctoscope labeled with the general reference character 10.

Proctoscope 10 is used to inspect the anal duct and the rectum, and for the surgical removal of tumors in the rectum.

Proctoscope 10 has a shaft 11 and a tube 12 in the form of a substantially cylindrical pipe. Attached to tube 12 is a handle 14 in the form of a hexagonal rod. Handle 14 can be inserted into a mount (not shown here) and immobilized therein.

Shaft 11 is embodied as insert 16 that is slid into tube 12. In the completely slid-in position of insert 16 shown in FIGS. 1 through 4, a distal end 18 of insert 16 projects axially out of tube 12. A proximal end 20 of insert 16 is rotatably attached to a proximal end 22 of tube 12. Proximal end 22 of tube 12 is embodied, for that purpose, as a cone flaring in the proximal direction, over whose rim an annular flange 24 of insert 16 is slid. Arranged in annular flange 24 is an attachment means 25 that has a clamping piece 26 and a turning knob 27 joined thereto. In order to attach insert 16 to tube 12, clamping piece 26 is rotated over the conical proximal end 22 of tube 12. Insert 16 is thereby axially immobilized in tube 12, but can be rotated through a full circle in tube 12.

To rotate insert 16 in tube 12, a large knurled wheel 28 joined immovably to insert 16 is arranged thereon.

Proctoscope 10 furthermore has an endoscopic optical system 30. Endoscopic optical system 30 has an eyepiece 32 at the proximal end of the proctoscope. Endoscopic optical system 30 is slid into a conduit 34 and can be removed therefrom. Conduit 34 is immovably joined to insert 16. Conduit 34 passes through insert 16 and ends, in the region of distal end 18 of insert 16, in a conduit opening 36. When endoscopic optical system 30 is slid in, its lens 39 is located in conduit opening 36. Conduit opening 36 is located at the proximal end of a cutout 37 configured in distal end 18 of insert 16. Conduit opening 36 and thus lens 39 of endoscopic optical system 30 are thus offset slightly in the proximal direction with respect to the outermost distal end.

Arranged at the proximal end of conduit 34 is an optical coupling 38 which has an optical system interlock 40 so as to lock endoscopic optical system 30 in conduit 34 and thus on insert 16. In addition, a connector 42 for connecting a light guide (not shown here) is provided in the region of eyepiece 32.

Figures 1, 2:
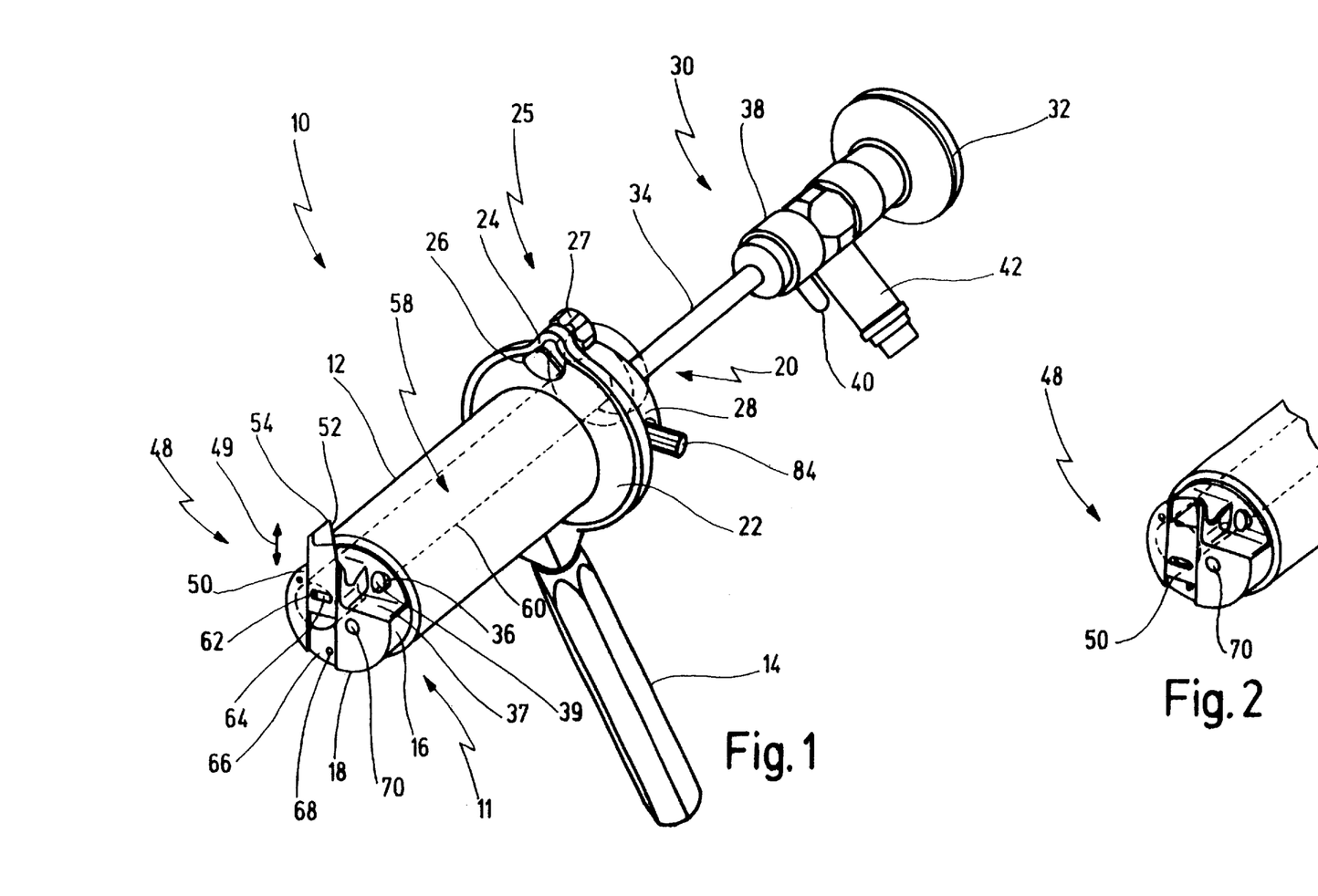
FIG. 1 shows a perspective view of an endoscopic instrument, embodied as a proctoscope, with the cutting tool extended, viewed from the distal end.
FIG. 2 shows the distal region of the proctoscope in FIG. 1, with the cutting tool retracted.

A cutting tool 48 that can be extended radially out of insert 16 and retracted back thereinto is arranged in the region of distal end 18 of insert 16. In FIG. 1 cutting tool 48 is shown in its extended position, while FIG. 2 shows cutting tool 48 in its retracted position. In the extended position according to FIG. 1, cutting tool 48 projects beyond the periphery of insert 16 and beyond the periphery of tube 12. In the retracted position shown in FIG. 2, cutting tool 48 is completely recessed into insert 16. A connectable drive system (not shown here), for example a rotary drive system with eccentric cam, provides for a back-and-forth oscillating movement of cutting tool 48 in the extended position, in a direction indicated with a double arrow 49.

Lens 39 of endoscopic optical system 30 is arranged with respect to cutting tool 48 behind it and offset slightly to the side. Lens 39 is moreover configured so that cutting tool 48 lies in the field of view of lens 39.

Figure 5:
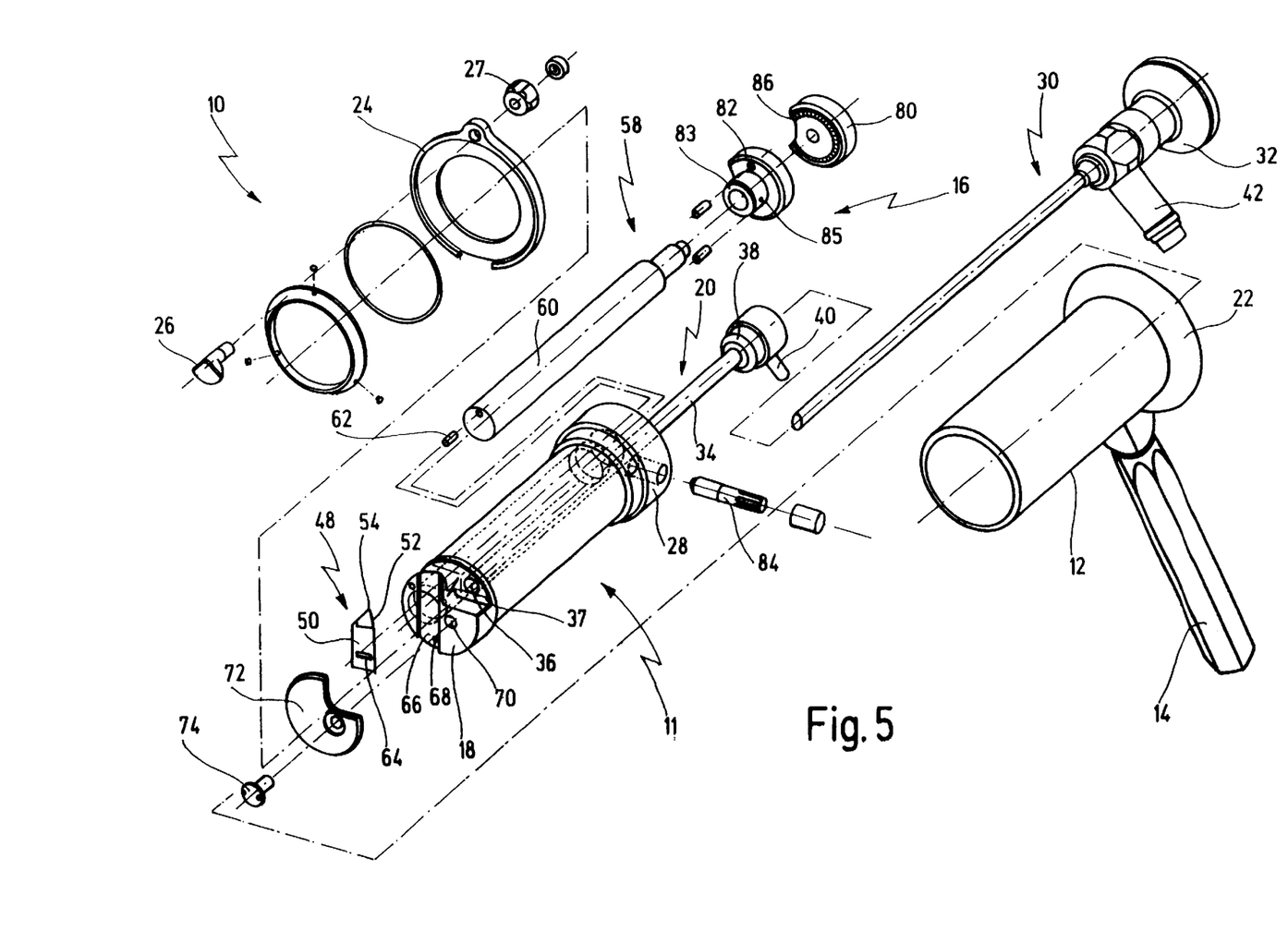
FIG. 5 shows an exploded view of the proctoscope in FIGS. 1 through 4.
Figure 6:
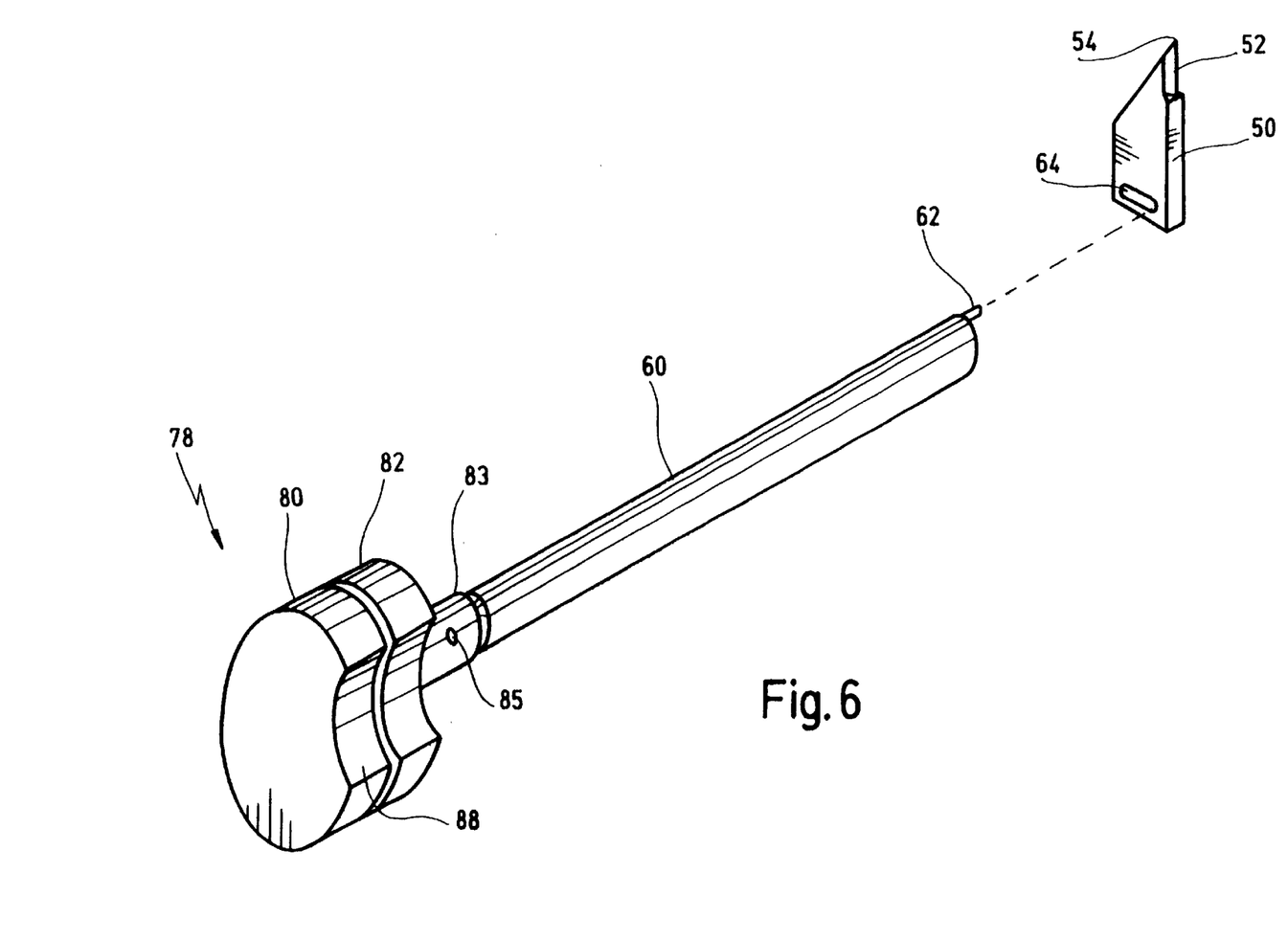
FIG. 6 shows a perspective detail view of an actuation rod and a cutting tool of the proctoscope in FIGS. 1 through 5.

Cutting tool 48 comprises a blade 50 that is configured substantially in the form of a thin metal plate (see FIGS. 5 and 6). Blade 50 has a cutting edge 52 and a tip 54. When blade 50 is in the extended state, cutting edge 52 faces in the circumferential direction of insert 16 (see FIG. 1).

Also provided, in order to retract and extend cutting tool 48, is a displacement mechanism labeled with the general reference character 58. Displacement mechanism 58 has an actuation rod 60 that can be slid into insert 16 and removed completely from it. Actuation rod 60 is shown in detail in FIGS. 5 and 6. At its distal end, actuation rod 60 has an axially projecting pin 62 arranged eccentrically with respect to the longitudinal axis. When actuation rod 60 is completely slid in, pin 62 engages into an elongated hole 64 cut out in blade 50.

Blade 50 is received in a recess 66 cut out at distal end 18 of insert 16, and is radially displaceable therein. The depth of recess 66 in the axial direction is exactly equal to the thickness of blade 50. Recess 66 passes substantially radially through distal end 18 of insert 16, and is thus open from periphery to periphery. In the region of the lower (in FIG. 1) periphery, a pin-shaped stop 68 for blade 50 is arranged in recess 66 in order to limit the radial displaceability of blade 50 against stop 68.

Figures 3, 4:
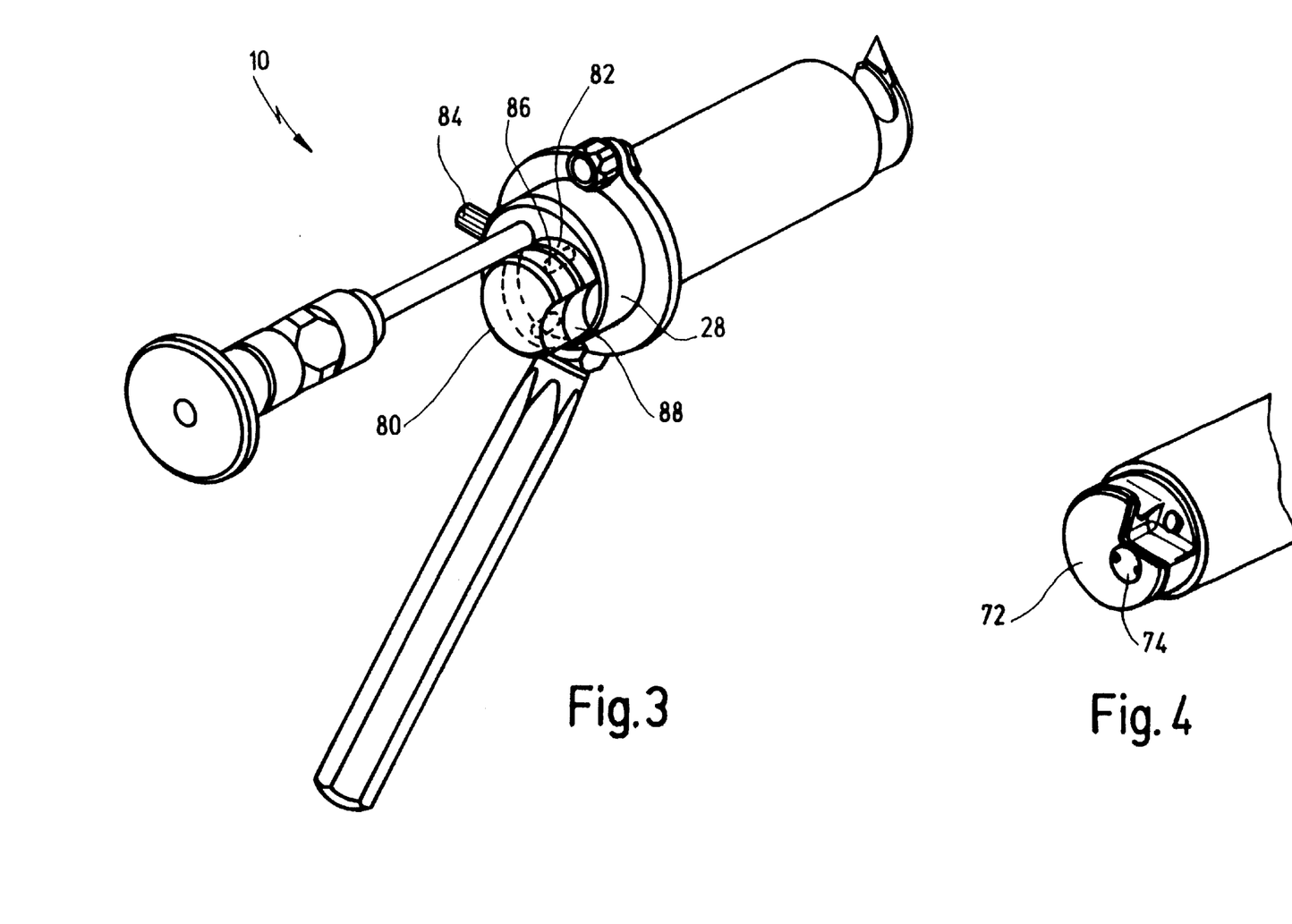
FIG. 3 shows a perspective view of the proctoscope in FIG. 1, viewed from the proximal end.
FIG. 4 shows the distal region of the proctoscope in FIGS. 1 through 3 with a distal covering.

In addition, a threaded hole 70, into which a cover 72 can be attached with a screw 74 in order to close off distal end 18 of insert 16, is provided at distal end 18 of insert 16, is as shown in FIG. 4. When cover 72 is closed, recess 66 together with cover 72 forms a slot in which blade 50 can move only radially.

At its proximal end, actuation rod 60 has two wheels 80 and 82 that are rotatable relative to one another, wheel 80 being joined nonrotatably to actuation rod 60, while wheel 82 is rotatable about the longitudinal axis of actuation rod 60. For that purpose, wheel 82 has an axial projection in the form of a sleeve 83 that is attached rotatably on actuation rod 60 (cf. FIG. 5).

A locking screw 84, with which wheel 82 of actuation rod 60 can be locked on insert 16, is arranged in large knurled wheel 28 of insert 16. Provided for that purpose in sleeve 83 of wheel 82 is a hole into which one end of locking screw 84 engages. When locking screw 84 is screwed in, actuation rod 60 is immobilized axially on insert 16, and in addition wheel 82 is immobilized nonrotatably on insert 16.

Several ball catches 86, constituted by two balls spring-mounted diametrically with respect to one another in wheel 82 and a plurality of corresponding cup recesses in wheel 80, are arranged between wheel 80 and wheel 82 (see FIG. 5). When wheel 80 is rotated while wheel 82 is at the same time immobilized, actuation rod 60 can be rotated to retract and extend blade 50; because of ball catches 86, wheel 80 and thus actuation rod 60 can be click-stopped in a plurality of rotational positions. Different rotational positions of wheel 80 result in different extension spans of blade 50, as will be explained below in further detail.

Also provided on wheel 80 is an indicating means in the form of a scale with which the rotational position and thus the extension span of blade 50 can be read off exactly. Additionally or alternatively, a scale indicating the particular extension span of blade 50 is present on blade 50.

In addition, an identical circular cutout 88 is configured in each of wheels 80 and 82.

The manner of operation of displacement mechanism 58 will now be described with reference to FIGS. 7a) and 7b).

Figure 7:
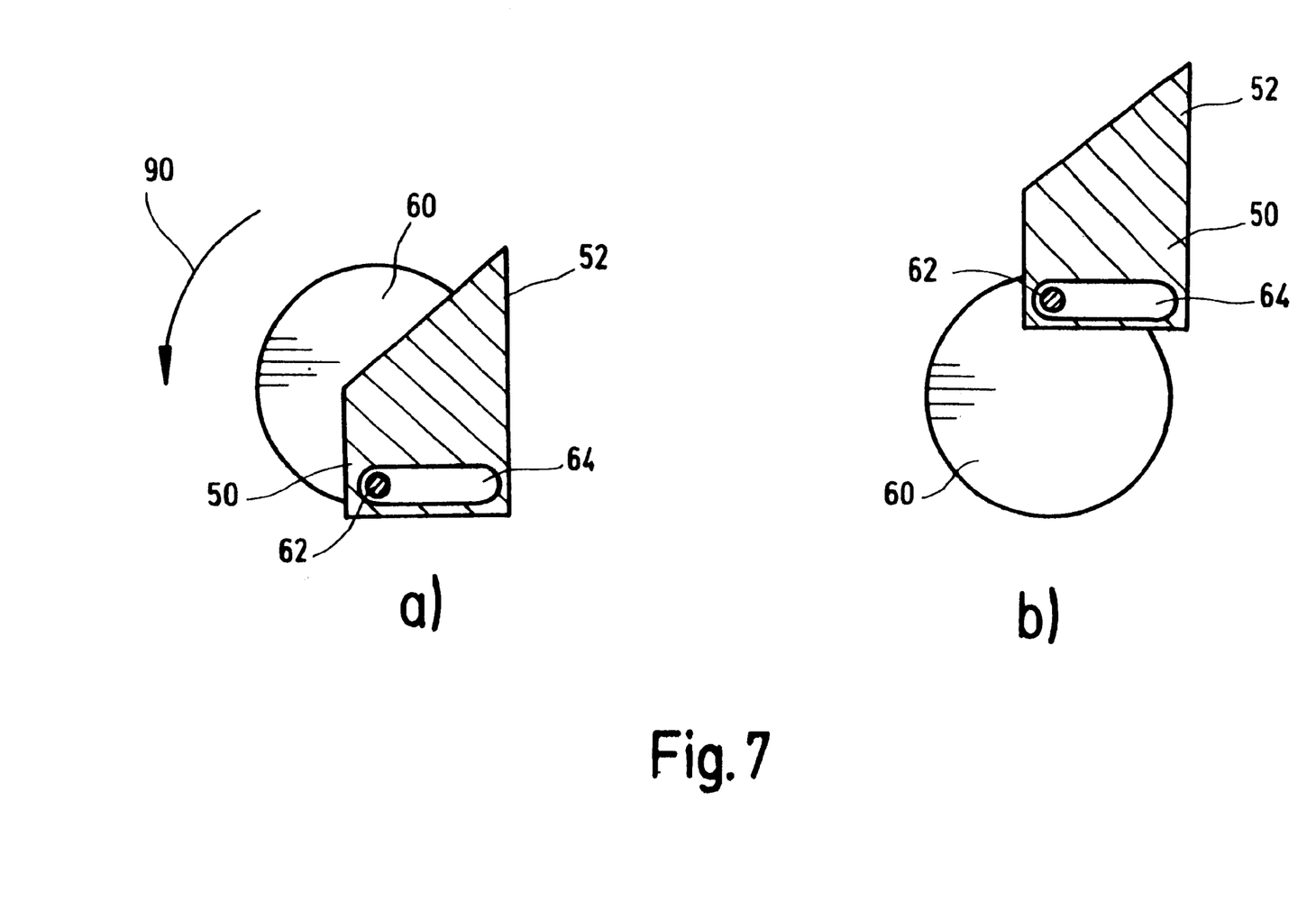

FIG. 7a) shows blade 50 in the completely retracted position as shown in FIGS. 2 and 4. When proctoscope 10 is completely assembled and ready to operate, pin 62 of actuation rod 60 engages, as already mentioned, into elongated hole 64 of blade 50. Blade 50 then rests on stop 68 in recess 66 (cf. FIG. 2). When actuation rod 60 is then rotated via wheel 80 in the direction of an arrow 90, blade 50 as a result extends out of recess 66 beyond the periphery of insert 16 and of tube 12; blade 50 is shown in FIG. 7b) in a position of maximum extension span. Blade 50 extends out of recess 66 in the radial direction. Between the completely retracted position shown in FIG. 7a) and the maximally extended position shown in FIG. 7b), blade 50 can assume any intermediate position with a different extension span; because of ball catches 86 between wheels 80 and 82, blade 50 can be click-stopped and thus locked in a plurality of positions with different extension spans. A rotation of wheel 80 through approximately 180° is required to bring blade 50 from the retracted position into the maximally extended position. Wheel 80 is turned back in the opposite direction in order to retract blade 50.

The manner in which proctoscope 10 is handled in a surgical operation will be described below.

Prior to use, insert 16, with endoscope optical system 30, displacement mechanism 58, and blade 50 in place, exists separately from tube 12. An obturator (not shown here in further detail) with a conical distal end is inserted into tube 12, and this arrangement of tube 12 and obturator is introduced into the patient's anal duct. The obturator is then pulled out of the tube, and insert 16 is introduced in place of the obturator. When insert 16 is slid in, cutting tool 48 (in this case blade 50) is in the completely retracted position, in which tip 54 of blade 50 does not project beyond the periphery of the insert. Insert 16 is slid completely into tube 12. Insert 16 is then attached to tube 12 with attachment means 25, by placing clamping piece 26 over the conical proximal end of the tube. By rotating large knurled wheel 28, the surgical field can be examined and adjusted through eyepiece 32. Proctoscope 10 is immobilized in the desired position with the retaining apparatus (not shown here) via handle 14. Blade 50 is extended by rotating wheel 80, and the incision can be made in circular fashion, parallel to the rim of proctoscope 10, by rotating insert 16 at large knurled wheel 28. As soon as the incision has been made, blade 50 is retracted back into insert 16 by rotating wheel 80 in the opposite direction until blade 50 is completely recessed. Insert 16 can then be pulled back out of tube 12.

During this procedure, irrigation takes place through a irrigation conduit (not shown) that extends through shaft 11 to cutting tool 48 and has a irrigation outlet there. Visibility during the operation can thereby be improved, so as to remove blood and tissue fragments from lens 39.

Optionally, especially in the case of an operation in body passages with a small diameter, for example the esophagus, a gaseous medium can be insufflated into the body passage via an insufflation conduit through shaft 11 in order to expand the duct and thus improve visibility.

Lastly, the disassembly of insert 16 and replacement of blade 50 will be described. Endoscopic optical system 30 is removed from insert 16 by loosening optical system interlock 40 and pulling endoscopic optical system 30 out of conduit 34 through optical system coupling 38.

Next, locking screw 84 is loosened. Actuation rod 60 is then pulled back in the proximal direction by approximately the length of sleeve 83, so that pin 62 disengages from elongated hole 64. Rotation of insert 16 hence causes blade 50 to fall out of the slot formed by recess 66 and cover 72. It is thus not necessary to remove cover 72 in order to take out blade 50. Actuation rod 60 can be pulled completely out of insert 16 when the circular cutouts 88 of the two wheels 80 and 82 are aligned with one another, since wheels 80 and 82, once endoscopic optical system 30 has been removed, can then be pulled in the proximal direction past optical system coupling 38 and out of insert 16.

To insert blade 50, first of all actuation rod 60 is introduced into insert 16 as far as sleeve 83. Blade 50 is then allowed to drop into recess 66, and is then supported on stop 68. Actuation rod 60 can then be slid completely into insert 16 by rotating actuation rod 60 until pin 62 is positioned at the same height as elongated hole 64. Actuation rod 60 can then be slid completely into insert 16 so that pin 62 engages into elongated hole 64, and locking screw 84 is screwed into hole 85 to lock wheel 82. Insert 16 is then ready for use.

What is claimed is:

1. An endoscopic instrument, having
   a shaft for introduction into a duct-like body passage, said shaft having a periphery,
   an endoscopic optical system extending through said shaft,
   a cutting tool arranged in said shaft,
      said cutting tool moveable between a retracted position where said cutting tool is completely recessed inside said shaft and an extended position where said cutting tool extends out of said shaft beyond said periphery of said shaft, and wherein in said extended position, said cutting tool is arranged for introducing an incision in said body passage in a circumferential direction,
      a displacement mechanism for moving said cutting tool between said retracted position and said extended position; and
      said cutting tool is a blade whose cutting edge is oriented in said circumferential direction of said periphery of said shaft.

2. The instrument of claim 1, wherein said cutting tool is lockable in a maximally extended position and in said retracted position.

3. The instrument of claim 2, wherein said cutting tool is lockable in a plurality of positions of different extension spans between said retracted position and said extended position.

4. The instrument of claim 1, wherein said cutting tool can be extended radially.

5. The instrument of claim 1, wherein said displacement mechanism is actuatable from a proximal end of said instrument.

6. The instrument of claim 1, wherein said displacement mechanism can be click-stopped for locking said cutting tool.

7. The instrument of claim 1, wherein said displacement mechanism has a proximally actuatable actuation rod whose distal end coacts with said cutting tool.

8. The instrument of claim 7, wherein said actuation rod is rotatable, and said cutting tool can be extended and retracted by rotating said actuation rod.

9. The instrument of claim 8, wherein a proximal end of said actuation rod has two wheels that are rotatable relative to one another, said one wheel being joined nonrotatably to said actuation rod and said other wheel being attachable nonrotatably on said shaft.

10. The instrument of claim 9, wherein one or more ball catches are arranged between said wheels.

11. The instrument of claim 1, wherein said displacement mechanism has a proximally actuatable actuation rod whose distal end coacts with said cutting tool, and said actuation rod is axially displaceable and said cutting tool can be extended and retracted by displacing said actuation rod.

12. The instrument of claim 1, wherein said displacement mechanism has a proximally actuatable actuation rod whose distal end coacts with said cutting tool, and said actuation rod is joined to said cutting tool by way of an axially detachable plug-in connection.

13. The instrument of claim 1, wherein a lens of said endoscopic optical system is arranged in the region of said cutting tool in such a way that said cutting tool is observable through said endoscopic optical system.

14. The instrument of claim 1, wherein in said extended position, said cutting tool can be caused to oscillate by way of a drive system.

15. The instrument of claim 1, wherein an indicating means for the extension span of said cutting tool is provided.

16. The instrument of claim 15, wherein said indicating means is provided on said cutting tool.

17. The instrument of claim 1, wherein an indicating means for the extension span of said cutting tool is provided and said indicating means is provided on said displacement mechanism.

18. The instrument of claim 1, wherein said blade tapers to a tip in the region of said cutting edge.

19. The instrument of claim 1, wherein said cutting tool is a blade whose cutting edge is oriented in said circumferential direction of said periphery of said shaft and said blade has an elongated hole into which engages a pin arranged at a distal end of said actuation rod eccentrically with respect to its longitudinal axis.

20. The instrument of claim 1, wherein said cutting tool is a blade whose cutting edge is oriented in said circumferential direction of said periphery of said shaft and said blade is received in a recess of said shaft that is open toward said periphery of said shaft and extends substantially radially.

21. The instrument of claim 1, wherein said shaft is configured as an insert that can be slid into a tube.

22. The instrument of claim 21, wherein said insert is attachable and rotatable in said tube.

23. The instrument of claim 1, wherein said shaft is flexible.

24. A method for introducing an incision into a wall of a duct-like body passage, comprising the steps of providing an instrument having a shaft for introduction into said duct-like body passage and a cutting tool disposed within said shaft that by way of a displacement mechanism can be extended out of said shaft beyond a periphery of said shaft, introducing said instrument with said cutting tool in its retracted position into said body passage such that said periphery of said shaft is positioned at a portion of said wall where said incision is to be introduced, extending said cutting tool beyond said periphery of said shaft by way of said displacement mechanism whereby said cutting tool engages said wall, turning said shaft about its longitudinal axis thereby introducing said incision into said wall of said body passage in a circumferential direction.

25. The method of claim 24, wherein said cutting tool is retracted back into said shaft before removing said instrument from the body passage.

26. The method of claim 24, wherein the steps of introducing said instrument into said body passage and turning said shaft for introducing said incision into said wall of said body passage are endoscopically monitored by viewing through an endoscopic optical system of said instrument.

27. The method of claim 24 including the further step of irrigating a fluid through said shaft into the surgical area when said instrument is introduced in said body passage.

28. The method of claim 24 including the further step of insufflating a gas through said shaft into the body passage for expanding the duct.

* * * * *